United States Patent [19]
Castaneda

[11] Patent Number: 5,460,614
[45] Date of Patent: Oct. 24, 1995

[54] GUIDEWIRE TRAPPING CATHETER

[75] Inventor: Javier E. Castaneda, Maimi, Fla.

[73] Assignee: Cordis Corporation, Miami Lakes, Fla.

[21] Appl. No.: 290,608

[22] Filed: Aug. 15, 1994

[51] Int. Cl.$^6$ .......................... A61M 5/178; A61M 25/00; A61B 6/00
[52] U.S. Cl. .......................... 604/165; 604/280; 604/282; 128/658
[58] Field of Search ................ 604/93, 95, 165, 604/107, 264, 280, 281, 282; 128/656–658

[56] References Cited

U.S. PATENT DOCUMENTS

| | | |
|---|---|---|
| 4,748,982 | 6/1988 | Horzewski et al. |
| 4,762,129 | 8/1988 | Bonzel. |
| 5,040,548 | 8/1991 | Yock. |
| B1 4,762,129 | 7/1991 | Bonzel. |

*Primary Examiner*—John D. Yasko
*Assistant Examiner*—Adam J. Cermak
*Attorney, Agent, or Firm*—Gerstman, Ellis & McMillin, Ltd.

[57] ABSTRACT

An intravascular catheter comprises a flexible tubular catheter body having a guidewire lumen. A pull cord extends through the catheter from a first position adjacent the proximal end of the lumen to an end position of the lumen remote from the proximal end, typically adjacent the distal end, where the pull cord is attached to the catheter body. The pull cord defines at least one loop extending about the guidewire lumen. The pull cord is longitudinally movable relative to the catheter body except where it is attached thereto. Thus, pulling the cord from the first position can cause the pull cord loop to straighten and trap a guidewire occupying the lumen, to suppress longitudinal motion of the guidewire.

20 Claims, 1 Drawing Sheet

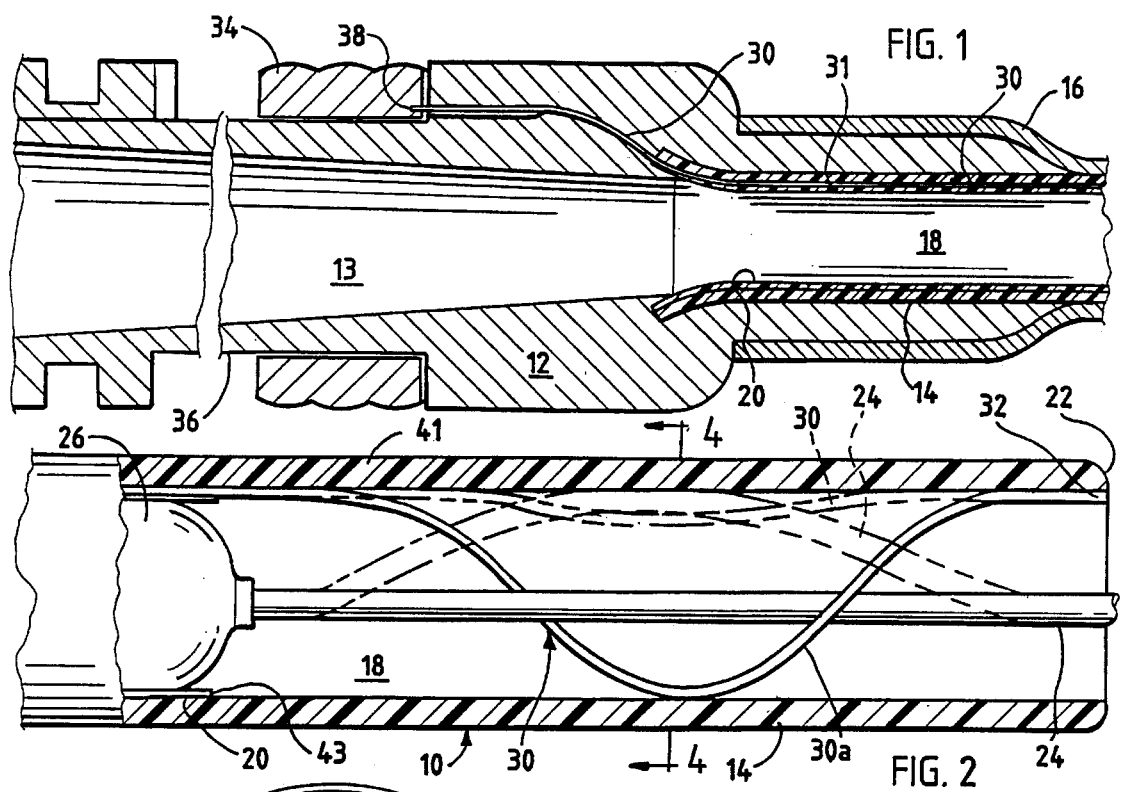
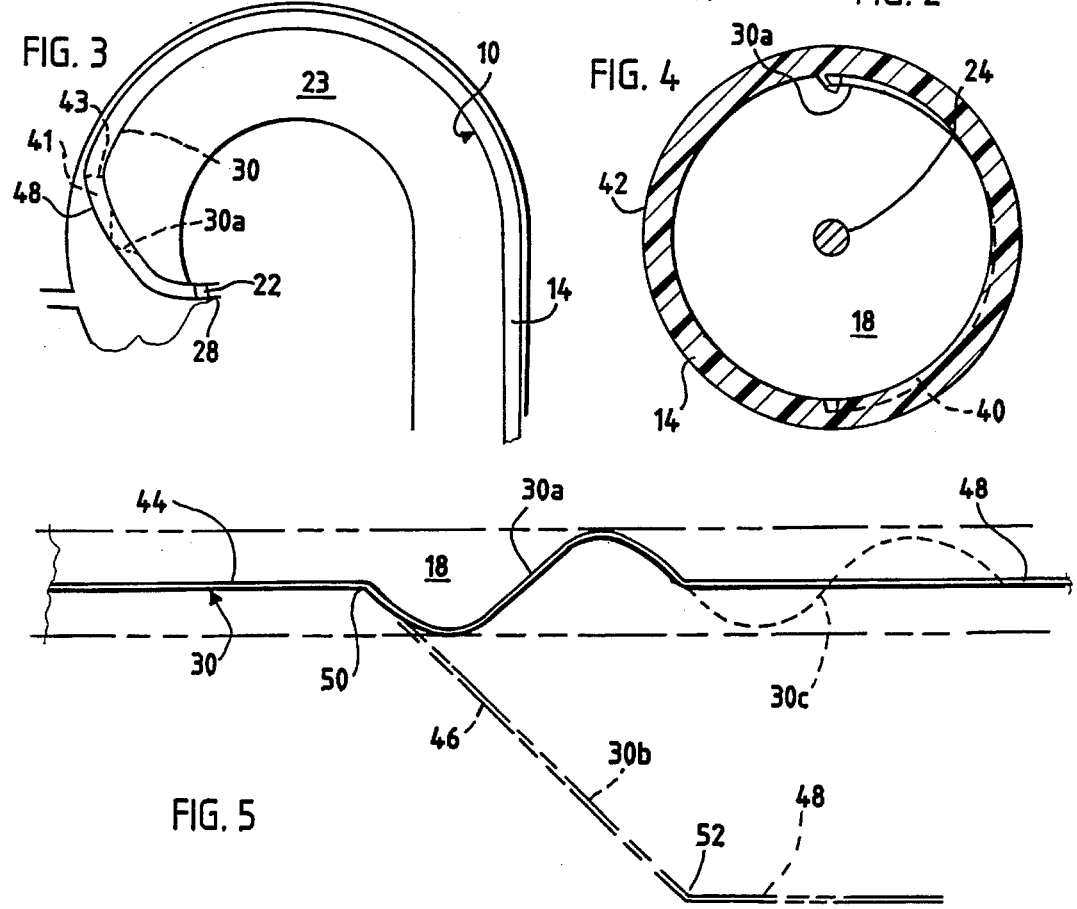

GUIDEWIRE TRAPPING CATHETER

BACKGROUND OF THE INVENTION

"Rapid exchange"-type balloon dilatation catheters are catheters which are capable of advancement into the vascular system of a patient along a preemplaced guidewire for balloon angioplasty or the like, in which a guidewire extension unit is not needed in order to remove the catheter without dislodging the guidewire. For example, in one type of rapid exchange catheter, the guidewire occupies a lumen of the catheter in only a distal portion thereof. With respect to the catheter proximal portion, the guidewire exits from the internal catheter lumen and extends along the side of the catheter, being typically retained in that position by a guiding catheter in which both the catheter and the guidewire are contained. Examples of catheters of this general type include those disclosed in Horzewski et al. U.S. Pat. No. 4,748,982; Bonzel U.S. Pat. No. 4,762,129; and Yock U.S. Pat. No. 5,040,548.

Such catheters permit one to replace the catheter without the use of a guidewire extension, which provides a more rapid exchange.

A disadvantage of such "rapid exchange" type catheter systems having a lateral aperture between the ends is that the guidewire cannot be removed for exchange while the catheter is indwelling in the patient. Furthermore, the reduced length of engagement between the guidewire and catheter can compromise the handling characteristics of the catheter. Likewise, the guidewire lumen of such catheters cannot be easily flushed with fluids to clear out obstructions and the like because of the side aperture.

In the conventional, over-the-wire intravascular catheter, the guidewire itself is easily exchanged after the catheter has been inserted. Also, the guidewire lumen is easily flushed with fluids in such a catheter design. However, this design does exhibit the disadvantage of generally requiring the attachment of a guidewire extension unit if one wishes to exchange the catheter.

By this invention, a catheter is provided which exhibits the advantages of the over-the-wire mode of operation, being suitable for use as a "guiding catheter", which is a conventional type of catheter used in angioplasty to receive both guidewire and a balloon catheter within its lumen. While the advantages of the over-the-wire catheter systems may be achieved, internal or balloon catheters may also be exchanged without a guidewire extension, and the guidewire itself may be exchanged with great ease.

Thus, the catheter of this invention can greatly facilitate intravascular procedures that utilize a catheter, particularly angioplasty procedures in which the catheter of this invention is used as the guiding catheter.

DESCRIPTION OF THE INVENTION

In accordance with this invention, an intravascular catheter is provided which comprises a flexible, tubular catheter body having a guidewire lumen with proximal and distal ends. A pull cord is provided, extending through the catheter from a first position adjacent the proximal catheter end to an end position which is remote from the proximal end, and is preferably positioned adjacent to the distal end of the catheter. The pull cord which is preferably a wire, is attached to the catheter body at this end position.

The pull cord defines at least one loop extending about the guidewire lumen. The pull cord is also longitudinally movable relative to the catheter body, except where the pull cord is attached to the catheter body. Thus, pulling of the pull cord from the first position can cause the pull cord loop to straighten and typically to be drawn against the wall of the catheter lumen. This can have the effect of trapping a guidewire which occupies the lumen, to suppress longitudinal motion of the guidewire.

Then, after the guidewire is so trapped against the catheter lumen wall, being held there by the tensioned pull cord, one can withdraw another catheter, which may be a balloon catheter and which also surrounds the guidewire and occupies the guidewire lumen, without dislodging the guidewire and moving it in a distal direction. Because the guidewire is so retained by the pull cord, the proximal end of the guidewire may be entirely enclosed within the withdrawing catheter without dislodging the guidewire from its advanced position in the vascular system of the patient.

As is well-known, it is most desirable to keep a guidewire in its maximum, advanced position in the vascular system, especially when it has penetrated through a stenosis. Withdrawal of the guidewire for any reason, even inadvertently and briefly, may result in the situation where it is not possible to advance the guidewire through that stenosis again. Thus the success of the surgical procedure may depend on being certain that the guidewire is not withdrawn during a catheter exchange, which certainty can be provided by this invention.

Preferably the pull cord comprises a metal wire, so that it may occupy a minimum diameter but still retain substantial strength and a measure of stiffness. Also, the pull cord is preferably carried in contact with the catheter body along essentially all of its length, at least in the initial condition of the pull cord, until it has been straightened by pulling. Then, some of the pull cord in the area of the loop may no longer be in contact with the catheter body i.e., the walls of the guidewire lumen, but it is generally preferred for the remainder of the pull cord to be retained in a channel such as a tunnel in the catheter wall, while being in sliding relation with the catheter wall.

For example, the tubular catheter body may carry a known thin, inner catheter tube made of polytetrafluoroethylene or the like for purposes of providing lubricity to the guidewire lumen. This thin, inner catheter tube may have a channel defined in the inner catheter tube, or outside of it if desired, extending from the pull cord loop toward the catheter proximal end. Thus the pull cord can occupy that channel in sliding relation, so that upon pulling, the loop or loops defined in the pull cord are straightened. Then, upon release of the tension on the pull cord, it may be possible for particularly a metal pull cord to spring back at least to a certain extent into its original configuration, to be ready to receive another catheter advanced along the guidewire through the reformed loop.

The catheter of this invention may define a curve adjacent to the catheter distal end, which curve is conventional for the purposes of steering of the catheter through the branching arterial system around the heart, or some other location. The channel which receives the pull cord may be positioned at the curve on the side of the catheter body that faces the direction of the curve with the loop portion being typically distal to the curve. Thus, on pulling of the pull cord, the guidewire may be held in the manner described above. Also, stability of the catheter curved tip may be increased in that the pull cord will tend to close or increase such a curve on such pulling, which will tend to hold the tip of the catheter in a desired branch of a coronary artery or the like.

The channel for the pull cord also may define a radially inwardly open portion that encloses the pull cord in the section of the pull cord which extends through the loop. Thus, upon pulling, the pull cord can be pulled out of such an inwardly open channel portion into a straightened form for trapping of the guidewire.

The pull cord may comprise a plurality of helical coils, typically two or three, which are positioned close together for more reliable and tight trapping of the guidewire.

It is also desirable for the pull cord to comprise a straight metal wire which defines, in its unstressed condition, a pair of spaced, obtuse angle bends of typically about 120°–150°, so that the wire in its unstressed condition defines two parallel end sections and a central, obtuse angle section of the pull cord. The obtuse angle section, when placed in the guidewire lumen, forms the desired loop (or plurality of loops) in the guidewire lumen by the constraint which is imposed on the pull cord by the guidewire lumen. A pull cord of this shape is biased outwardly at the loop area, forming a helical loop or series of loops in the guidewire lumen, with the helical loops being biased with outward pressure so that they tightly hug the lumen wall, even in the absence of a retaining groove.

DESCRIPTION OF THE DRAWINGS

In the drawings, FIG. 1 is an enlarged, longitudinal sectional view of the proximal end of the catheter of this invention;

FIG. 2 is a longitudinal sectional view, with a portion shown in elevation, of the distal portion of the catheter of this invention;

FIG. 3 is a diagrammatic view of the catheter of FIGS. 1 and 2, with a distal portion of the catheter being shown occupying the aortic arch of a patient;

FIG. 4 is a sectional view taken along line 4—4 of FIG. 2; and

FIG. 5 is a diagrammatic view showing a wire pull cord of this invention as it is constrained while occupying the guidewire lumen of the catheter of FIGS. 1 and 2, and showing in phantom lines the natural, unstressed condition of the pull cord.

DESCRIPTION OF SPECIFIC EMBODIMENTS

Referring to the drawings, the catheter 10 of this invention is shown, being of a generally conventional design of an arterial guiding catheter except as otherwise indicated herein. Catheter 10 defines a proximal end having a tapered-bore hub 12 to fit with a conventional male luer connector in lumen 13. Hub 12 is connected to flexible tubular catheter body 14, with a connection being reinforced by a strain relief 16.

Catheter body 14 encloses, in this embodiment, a single lumen 18, although other embodiments may include other lumens as well. Lumen 18 is particularly defined in this embodiment by an inner sleeve 20 which is connected to catheter body 14, and may be made of polytetrafluoroethylene (PTFE). Such a sleeve 20 is generally conventional, and is provided as a friction-reducing aid.

As is further conventional, FIG. 2 shows an enlarged, transverse sectional view of the distal end 22 of catheter 10, showing a conventional guidewire 24 extending through lumen 18, and also showing the distal end of a balloon catheter 26 occupying lumen 18. As is conventional, balloon catheter 26 is advanced through guiding catheter 10 along the preemplaced guidewire 24. Guidewire 24 facilitates the advancement of balloon catheter 26, which may be smaller, thinner, and more flexible than the guiding catheter 10, and thus less easily advanced through larger arteries. Balloon catheter 26 may then be advanced a certain distance out of and beyond the distal end 22 of guiding catheter 10, to be advanced through a branch artery, for example, to place the balloon of catheter 26 into a stenosis for expansion thereof in a conventional manner.

In accordance with this invention, a mechanism is provided by which balloon catheter 26 may be quickly withdrawn from guiding catheter 10 without disturbing the position of guidewire 24, which typically may be advanced to pass through the stenosis prior to the advancement of balloon catheter 26.

Guiding catheter 10 is shown in FIG. 3 to be in an emplaced position within the aortic arch 23 of a patient. Distal tip 22 of the guiding catheter 10 is shown to be emplaced in a coronary artery 28, to permit the advancement of balloon catheter 26 out of the distal end 22, farther into coronary artery 28, to reach the desired stenosis for treatment. This is facilitated by the conventional, curved distal end of guiding catheter 10 as shown in FIG. 3.

If the need arises to replace one balloon catheter 26 for another (for example because the balloon is an improper size for dilating the particular stenosis), this can be accomplished by this invention without the need for attachment of a guidewire extension to the proximal end of guidewire 24. Also, this can be accomplished by this invention without providing any side apertures or slits in catheter body 14. The absence of apertures facilitates the administration of an x-ray contrast fluid through the distal end of catheter 10 without side leakage.

To accomplish this replacement of catheter 26, a pull cord 30 is provided in catheter lumen 18, the pull cord being distally attached to catheter body 14 at a sealed attachment site 32, which may be adjacent the distal catheter end 22. Pull cord 30 is attached at its proximal end to a sliding handle 34, which is shown in FIG. 1 to be in its forward position, but which can be moved by sliding to a rearward position. Sliding handle 34 may be a ring as shown in this present embodiment, while a central portion 36 of the diameter of the hub portion along which ring 34 slides may be of slightly larger diameter than the end portions thereof. Thus, ring 34 may be retained either in the forward position as shown or a rearward position, while passing through a position of sliding resistance in intermediate positions that tends to hold sliding member 34 in either the fully advanced or fully retracted position.

Sliding handle 34 is connected to pull wire 30 at point 38. Thus, as sliding handle 34 is retracted, pull wire 30 is retracted with it.

Along most of the length of catheter body 14, pull wire 30 may reside in a passageway 31 which is defined between catheter body 14 and inner PTFE sleeve 20, in which pull wire 30 is positioned in sliding manner. This may be accomplished in any desired way in which the pull wire channel or passageway 31 is defined primarily by the outer catheter body 14, or defined primarily by the inner sleeve 20, or completely defined within inner sleeve 20 in a slightly thickened section of the catheter wall along a flattened surface facing lumen 18, if desired.

Near the distal end 22, inner sleeve 20 preferably terminates, with pull wire 30 extending distally beyond inner sleeve 20 into distal section 41, so that catheter body 20 is directly exposed to the interior of lumen 18. Referring to FIGS. 3 and 4 particularly, a helical channel 40 is defined in the inner wall of catheter body 14, with pull wire 30 occupying this channel and being firmly positioned against inner wall 42 of catheter body 14. Pull wire 30 defines at this point a helical section 30a, defining the loop or loops described above. The helical section 30a of pull wire 30 may occupy the helical groove 40.

Alternatively, helical groove 40 may be eliminated, while the helical section 30a of pull wire is naturally biased outwardly against the inner wall of catheter body 14. This biasing can particularly be accomplished if a pull wire 30 is used having a configuration as shown in FIG. 5. The pull wire 30 is schematically illustrated in an alternate configuration shown partly in broken lines, in which the pull wire occupies its unstressed condition. In this unstressed shape, three generally straight wire sections 44, 46, 48 are defined, being respectively separated by two obtuse angle bends 50, 52.

Pull wire 30 desirably is flexible, as is a typical wire, but with an amount of self supporting, shape-retaining capability. Thus, when such a pull wire is inserted into catheter lumen 18, the central section 30b becomes the helical section 30a, being biased into that shape by the constraint provided in lumen 18. Section 48 comprises a desired distal segment which is generally straight. If desired, one or more extra helical loops 30c can be provided in this manner, depending upon the length of central, straight section 30b, so that a plurality of loops may be provided to the pull wire in accordance with this invention.

Thus, when catheter 10 is emplaced as shown in FIG. 3, and a balloon catheter 26 is desired to be removed from the catheter 10 in a rapid manner without the use of a guidewire extension, the balloon catheter 26 may be withdrawn to approximately the position illustrated in FIG. 2. Then, sliding member 34 may be moved proximally (rearwardly) from the position shown in FIG. 1, to cause the proximal movement of pull wire 30 along the entire catheter. This, in turn, causes pull wire 30 to flatten itself against the inner wall of catheter body 14 at loop 30a, and loop 30c if that is present, as shown in broken lines in FIG. 2. This, in turn, causes guidewire 24 to be pulled by pull wire 30 into frictional contact with wire 30 and the wall of catheter body 14, providing retention of guidewire 24 which resists the withdrawing of the guidewire as catheter 26 is withdrawn. Thus, it becomes possible to remove the catheter 26 even though the proximal end of the guidewire becomes completely enclosed in the catheter, so that the main source of retention of the guidewire in its desired position is provided by the "trapping" imparted by pull wire 30.

Better trapping can be achieved when a plurality of loops 30a, 30c of pull wire 30 are used, as indicated in FIG. 5.

It is generally preferable for the catheter segment 41, which is distal to the end 43 of inner PTFE sleeve 20, to be transparent, so that the position of loop or loops 30a of the pull wire can be checked before use.

Also, it is preferred for pull wire 30 to be positioned in a portion of the wall of catheter 10 which is on the side of catheter body 14 that faces the direction of the curve 48. In other words, pull wire 30 is positioned adjacent the concave surface defined by curve 48. An advantage of this is that as pull wire 30 is pulled, the tension in the pull wire tends to increase curve 48 of the catheter through which pull wire 30 extends. That in turn tends to increase the holding power of distal tip 22 in the desired coronary artery 28.

Thus by this invention a catheter is provided with a guidewire trapping capability, which eliminates the need for side apertures or a guidewire extension when there is a need to stabilize the guidewire in its position of advancement during the withdrawal of an inner catheter.

The above has been offered for illustrative purposes only, and is not intended to limit the scope of the invention, which is as defined in the claims below.

That which is claimed:

1. An intravascular catheter which comprises a flexible, tubular catheter body having a guidewire lumen with proximal and distal ends, and a pull cord extending through said catheter from a first position adjacent the proximal end to an end position remote from the proximal end and attached to said catheter body, said pull cord defining at least one loop extending about said guidewire lumen, said pull cord being longitudinally movable relative to said catheter body except where the pull cord is attached to the body, whereby pulling said cord from said first position causes said pull cord loop to straighten and trap a guidewire occupying said lumen, to suppress longitudinal motion of said guidewire.

2. The catheter of claim 1 in which said pull cord comprises a metal wire.

3. The catheter of claim 1 in which the pull cord is carried in contact with said catheter body along essentially all of its length.

4. The catheter of claim 1 in which said tubular catheter body carries a thin, inner catheter tube defining said guidewire lumen, and a channel defined in at least said inner catheter tube and extending from said loop toward said catheter proximal end, said pull cord occupying said channel.

5. The catheter of claim 4 in which said channel defines a radially inwardly open portion that encloses said pull cord extending in said loop.

6. The catheter of claim 4 in which said catheter defines a curve adjacent to the catheter distal end, said channel being positioned at said curve on the side of said catheter body that faces the direction of said curve.

7. The catheter of claim 1 in which a section of said catheter body which encloses said loop is transparent.

8. The catheter of claim 1 further comprising guidewire, and a balloon catheter surrounding said guidewire, in said lumen.

9. The catheter of claim 1 in which the loop of said pull cord comprises a plurality of helical coils.

10. The catheter of claim 1 in which said pull cord comprises a straight metal wire which defines in its unstressed condition a pair of spaced, obtuse angle bends to define two parallel end sections and a central, obtuse angle section in said pull cord, said obtuse angle section forming said loop in said guidewire lumen by a constraint imposed on the pull cord by said guidewire lumen.

11. The catheter of claim 1 in which said pull cord end position of attachment to the catheter body is adjacent said distal end.

12. An intravascular catheter which comprises a flexible, tubular catheter body having a guidewire lumen with proximal and distal ends, and a metal wire pull cord extending through said catheter from a first position adjacent the proximal end to an end position remote from the proximal end and attached to said catheter body, said pull cord defining a plurality of loops extending about said guidewire lumen, said pull cord being longitudinally movable relative to said catheter body except where the pull cord is attached to the body, whereby pulling said cord from said first position causes said pull cord loops to straighten and trap a guidewire occupying said lumen, to suppress longitudinal motion of said guidewire.

13. The catheter of claim 12 in which the pull cord is carried in contact with said catheter body along essentially all of its length.

14. The catheter of claim 13 in which said tubular catheter body carries a thin inner catheter tube defining said guidewire lumen, and a channel defined between said inner catheter tube and said catheter body extending from said loop toward said catheter proximal end, said pull cord occupying said channel.

15. The catheter of claim 14 in which said channel defines a radially inwardly open portion that encloses said pull cord in said loop.

16. The catheter of claim 14 in which said catheter defines a curve adjacent to the catheter distal end, said channel being positioned at said curve on the side of said catheter body that faces the direction of said curve.

17. The catheter of claim 16 in which a section of said catheter body which encloses said loops is transparent.

18. The catheter of claim 12 further comprising a guidewire, and a balloon catheter surrounding said guidewire, in said lumen.

19. The catheter of claim 12 in which said pull cord comprises a straight metal wire which defines, in its unstressed condition, a pair of spaced, obtuse angle bends to define two parallel end sections and a central obtuse angle section in said pull cord, said obtuse angle section forming said loops in said guidewire lumen by a constraint imposed on the pull cord by said guidewire lumen.

20. The catheter of claim 12 in which said pull cord end position of attachment to the catheter body is adjacent said distal end.

* * * * *